United States Patent
Opsal

(10) Patent No.: US 7,400,403 B2
(45) Date of Patent: *Jul. 15, 2008

(54) BEAM PROFILE ELLIPSOMETER WITH ROTATING COMPENSATOR

(75) Inventor: Jon Opsal, Livermore, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/715,584

(22) Filed: Mar. 8, 2007

(65) Prior Publication Data

US 2007/0159630 A1    Jul. 12, 2007

Related U.S. Application Data

(63) Continuation of application No. 11/269,204, filed on Nov. 8, 2005, now Pat. No. 7,206,070.

(60) Provisional application No. 60/627,824, filed on Nov. 15, 2004.

(51) Int. Cl.
*G01J 4/00* (2006.01)

(52) U.S. Cl. .................................... 356/369

(58) Field of Classification Search ............. None
See application file for complete search history.

(56) References Cited

U.S. PATENT DOCUMENTS

| | | | |
|---|---|---|---|
| 4,999,014 A | 3/1991 | Gold et al. | 356/632 |
| 5,042,951 A | 8/1991 | Gold et al. | 356/369 |
| 5,166,752 A | 11/1992 | Spanier et al. | 356/369 |
| 5,181,080 A | 1/1993 | Fanton et al. | 356/632 |
| 5,412,473 A | 5/1995 | Rosencwaig et al. | 356/351 |
| 5,596,411 A | 1/1997 | Fanton et al. | 356/369 |
| 5,877,859 A | 3/1999 | Aspnes et al. | 356/364 |
| 5,889,593 A | 3/1999 | Bareket | 356/445 |
| 5,910,842 A | 6/1999 | Piwonka-Corle et al. | 356/369 |
| 6,268,916 B1 | 7/2001 | Lee et al. | 356/369 |
| 6,278,519 B1 | 8/2001 | Rosencwaig et al. | 356/369 |
| 6,429,943 B1 | 8/2002 | Opsal et al. | 356/625 |
| 6,483,580 B1 | 11/2002 | Xu et al. | 356/300 |
| 6,678,046 B2 | 1/2004 | Opsal | 356/369 |
| 6,822,738 B1 | 11/2004 | Johs et al. | 356/369 |
| 6,937,341 B1 * | 8/2005 | Woollam et al. | 356/436 |
| 7,075,055 B2 | 7/2006 | Nagai | 205/225 |
| 7,161,679 B2 * | 1/2007 | Messerschmidt et al. | 356/455 |

(Continued)

OTHER PUBLICATIONS

P. Boher et al., "Innovative Rapid Photo-goniometry method for CD metrology," *Metrology, Inspection, and Process Control for Microlithography XVIII, Proceedings of SPIE*, vol. 5375 (2004), pp. 1302-1312.

(Continued)

*Primary Examiner*—Tu T Nguyen
(74) *Attorney, Agent, or Firm*—Stallman & Pollock LLP

(57) ABSTRACT

An optical inspection device includes a light source for generating a probe beam. The probe beam is focused onto a sample to create a spread of angles of incidence. After reflecting from the sample, the light is imaged onto a two dimensional array of photodetectors. Prior to reaching the detector array, the beam is passed through a rotating compensator. A processor functions to evaluate the sample by analyzing the output of the photodetectors lying along one or more azimuthal angles and at different compensator positions.

24 Claims, 1 Drawing Sheet

U.S. PATENT DOCUMENTS

| | | | |
|---|---|---|---|
| 7,206,070 B2 * | 4/2007 | Opsal | 356/369 |
| 2001/0051856 A1 | 12/2001 | Niu et al. | 702/57 |
| 2002/0093656 A1 * | 7/2002 | Takeuchi et al. | 356/394 |
| 2004/0004726 A1 | 1/2004 | Sezginer et al. | 356/601 |
| 2004/0070772 A1 | 4/2004 | Shchegrov et al. | 356/625 |
| 2005/0041258 A1 | 2/2005 | Opsal et al. | 356/601 |
| 2005/0248773 A1 | 11/2005 | Rosencwaig | 356/504 |

OTHER PUBLICATIONS

J. Petit et al., "A new analysis strategy for CD metrology using rapid photo goniometry method," *Metrology, Inspection, and Process Control for Microlithography XVIII, Proceedings of SPIE*, vol. 5375 (2004), pp. 210-221.

* cited by examiner

BEAM PROFILE ELLIPSOMETER WITH ROTATING COMPENSATOR

PRIORITY CLAIM PROVISIONAL

This application is a continuation of U.S. patent application Ser. No. 11/269,204, filed Nov. 8, 2005, now U.S. Pat. No. 7,206,070, which in turn claims the benefit of U.S. Provisional Application No. 60/627,824, filed Nov. 15, 2004, both of which are incorporated herein by reference.

TECHNICAL FIELD

The subject invention relates to an optical metrology tool for inspecting and evaluating semiconductor wafers. The preferred embodiment is particularly suited for measurement of samples that are anisotropic about the axis of the probing beam.

BACKGROUND

There is considerable interest in monitoring properties of semiconductors at various stages during the fabrication process. Monitoring the properties during fabrication allows the manufacturer to spot and correct process problems prior to the completion of the wafer.

Inspection of actual product wafers during or between process steps usually require non-contact techniques. Accordingly, a number of tools have been developed for optically inspecting semiconductor wafers. Such tools include reflectometers and ellipsometers. To increase the robustness of the measurements, these tools can often obtain measurements at multiple wavelengths and/or multiple angles of incidence.

Therma-Wave, Inc., the assignee of the subject invention has developed a number of such tools over the last fifteen years. One of the first such tools is described in U.S. Pat. No. 4,999,014. In this tool, a probe beam from a laser is tightly focused on the sample with a high numerical aperture lens to create light rays with a spread of angles of incidence. The reflected beam is imaged onto an array detector. The location of the elements on the array detector can be mapped to different angles of incidence on the sample. Thus, this device can obtain reflectometry information at multiple angles of incidence with no moving parts. This configuration is still in commercial use today in Therma-Wave's Opti-Probe product line and is referred to as Beam Profile Reflectometry® or BPR®.

This concept was subsequently extended to ellipsometric measurement as described in U.S. Pat. No. 5,042,951. In this approach, the change in polarization state of the probe beam is monitored at multiple angles of incidence. Various polarizers and a waveplate (or compensator) are used to permit the polarization analysis. A variant of this approach which integrates the angular information is disclosed in U.S. Pat. No. 5,181,080. This configuration is also in commercial use and is referred to as Beam Profile Ellipsometry® or BPE®.

While the latter patents were directed primarily to single wavelength systems, efforts have been made to extend these concepts to multiple wavelength systems. See for example, U.S. Pat. Nos. 5,412,473 and 5,596,411.

The assignee herein has also made efforts to improve broadband spectroscopic ellipsometry. More specifically, and as described in U.S. Pat. No. 5,877,859, an improved spectroscopic ellipsometer was proposed that utilized a rotating compensator (waveplate). Prior to this disclosure, rotating compensators were typically used only in narrow band ellipsometers, while rotating polarizers were used in broadband, spectroscopic ellipsometers. U.S. Pat. No. 5,877,859 discloses how a rotating compensator can be used in BPR and BPE type systems.

The photodetectors used in the basic BPR and BPE systems usually were defined by two linear arrays of photodetector elements oriented orthogonally to each other. Some of the above cited patents suggest that a two dimensional CCD array could be used. In some cases, the CCD array was used to measure both wavelength and angle of incidence information. The use of a CCD array in conjunction with various types of BPE measurements was proposed in U.S. Pat. No. 6,678,046 and in U.S. patent application No. 2005/0041258.

Each of the above cited patents and patent application are incorporated herein by reference. Also relevant are U.S. Pat. Nos. 6,278,519; 6,429,943; 5,166,752, 5,889,593; 5,910,842; 6,268,916; 6,483,580; 2001/0051856; 2004/0004726 and 2004/0070772 each of which is incorporated herein by reference.

SUMMARY OF THE INVENTION

The subject invention is an optical metrology tool and represents another variant on the Beam Profile Ellipsometry technology. In one preferred embodiment, a polarized probe beam is focused onto the sample using a high numerical aperture lens to create a spread of angles of incidence. The beam is passed through a rotatable compensator (waveplate). By using a rotatable compensator, the analyses of the type described in U.S. Pat. No. 5,877,859 can be used. The reflected probe beam is directed to a two-dimensional array detector such as a CCD.

A processor analyzes the output from the detector. The processor is arranged to evaluate the output of the CCD detector along one or more azimuthal directions. Evaluating the output along multiple azimuthal directions is particularly useful when the sample is not isotropic about the axis of the probing beam. In this case, measurements along one azimuthal direction will contain information about the sample that is independent from that contained along another axis.

Historically, optical metrology systems of this type were used to evaluate the parameters of multi-layer thin film dielectrics formed on the surface of a silicon substrate. These samples tended to be isotropic about the axis of the probing beam. More recently, efforts have been made to optically measure micron size geometrical features (critical dimension analysis) such as gratings, grids of vias or holes, isolated lines, trenches, etc. These structures tend to be anisotropic about the axis of the probing beam and could be more accurately analyzed using the approaches discussed herein.

The processor can be used to map the location of the individual detector elements to specific angles of incidence. Alternatively, an integrated approach can be used where the output of arrays along particular azimuthal axes are summed in the manner described in U.S. Pat. No. 6,429,943 cited above.

Various approaches can be utilized to obtain information at more than one wavelength. For example, multiple lasers each generating a different wavelength output could be activated sequentially. Alternatively, a white light source and a color filters or a monochrometer could be used to scan the wavelengths.

Further features of the subject invention will be discussed in conjunction with the drawings in which:

DETAILED DESCRIPTION OF THE PREFERRED EMBODIMENT

Figure 1:
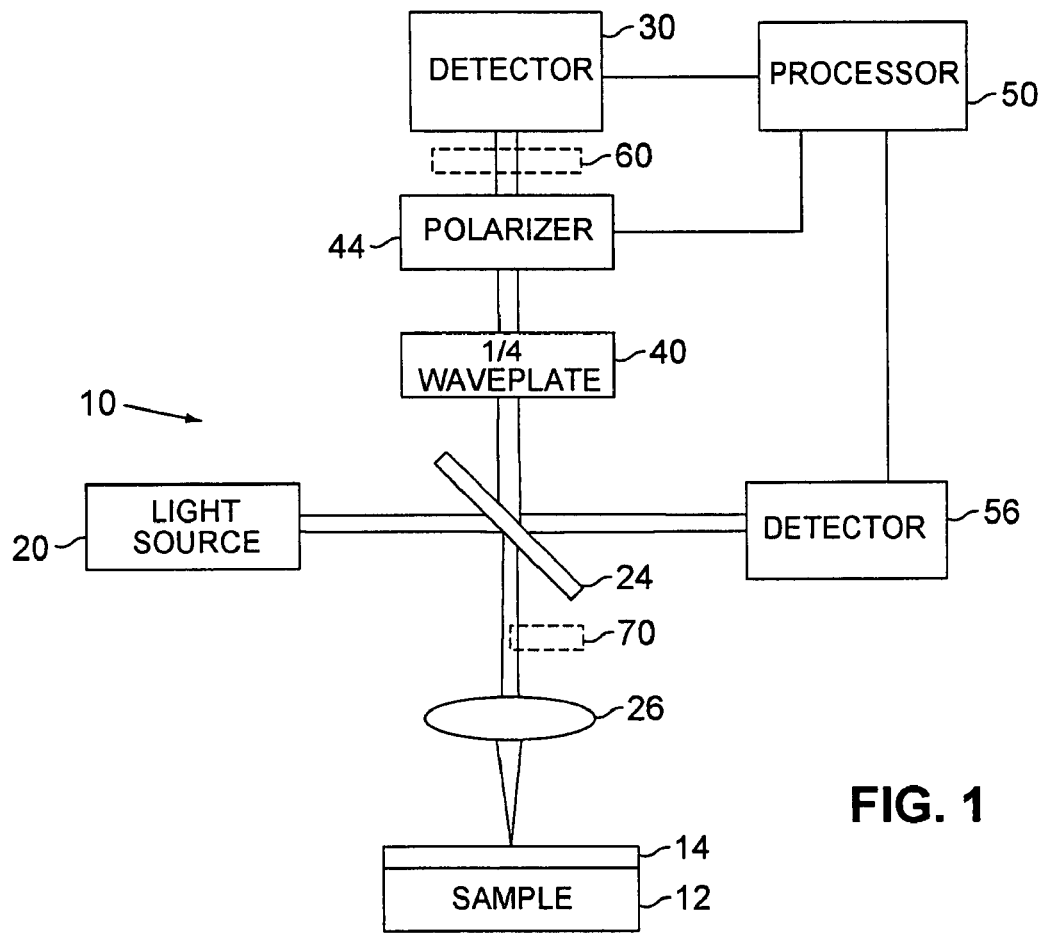
FIG. 1 is a schematic diagram of the optical metrology tool configured in accordance with the subject invention.

Turning to FIG. 1, an apparatus 10 configured in accordance with the subject invention is illustrated. Apparatus 10 is intended to be used to evaluate a sample 12 having one or more layers 14 formed thereon. Typically, layers 14 can be dielectric or metal layers. In addition, various features can be formed into the layers such as periodic line space structures (gratings), vias, holes, aperiodic structures and isolated structures. The geometric structures in particular tend to introduce anisotropies in the surface that can be more easily measured with the device of the subject invention.

Apparatus 10 includes a light source 20 for generating a probe beam 22. In one preferred embodiment, light source 20 is a laser generating a stable narrow wavelength beam. Other variants for the light source will be discussed below. In one preferred embodiment, the output of light source 20 is polarized. Alternatively, a polarizer can be placed in the path of the beam to provide polarization control.

Probe beam 22 is directed towards the sample, in this case, by beam splitter 24. The beam is focused onto the sample with a focusing element 26. Focusing element 26 should have a relatively high numerical aperture to create a large spread of angles of incidence on the sample. Element 26 preferably has a numerical aperture of at least 0.5 and more preferably on the order of 0.9. A focusing element with an NA of 0.5 will create angles of incidence from zero to 30 degrees with respect to the normal. A 0.9 NA (or greater) will extend that range out to about 64 degrees (and beyond).

In a preferred embodiment, the focusing element 26 is a compound microscope objective. Element 26 can include lenses, mirrors or a combination of both. In one preferred embodiment, the probe beam is focused to a spot size on the order of 10 microns or less and in some cases more preferably on the order of about one micron in diameter.

Light reflected from the sample is collected by the lens 26 and directed to a photodetector 30. Prior to reaching detector 30, the probe beam 22 is passed through a compensator, in this case, quarter waveplate 40 for retarding the phase of one of the polarization states of the beam. It should be noted that the quarter-wave plate could be located in the beam path prior to the probe beam striking the sample. The latter approach might have some advantages in reducing the aberrations created by lens 26. In a preferred embodiment, the compensator induces a phase retardation of 90 degrees, however larger or smaller retardations are possible. In fact, retardations ranging from about 30 deg to 330 deg provide useful ellipsometric information as described in U.S. Pat. No. 5,877,859.

The beam is then passed through a linear polarizer 44 which functions to cause the two polarization states of the beam to interfere with each other. In order to maximize the desired signal, the axis of the polarizer can be oriented at an angle of 45 degrees with respect to the fast and slow axes of the quarter-wave plate 40. There may be situations depending on sample conditions where the optimal orientation of the polarizer would be somewhere between 30 degrees and 60 degrees with respect to the fast and slow axes of the quarter-wave plate.

Figure 2:
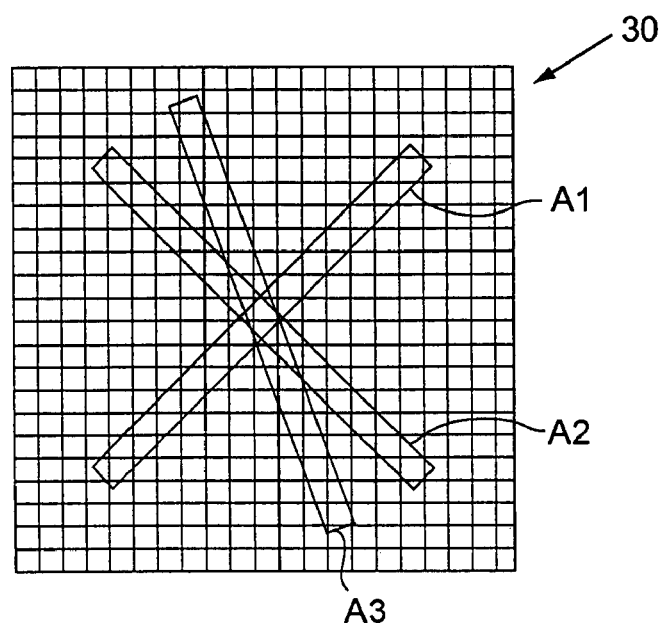
FIG. 2 is a layout of a two dimensional detector that can be used in the subject invention.

As illustrated in FIG. 2, detector 30 is preferably comprised of a two-dimensional array of photodetector elements or pixels 32. Such an arrangement is typical in commercially available CCD arrays. In a preferred embodiment, the arrays would have a minimum of 64 columns and 64 rows of elements. The output from the elements of detector 30 are supplied to a processor 50. Processor 50 also controls and monitors the position of waveplate 40 and in some cases polarizer 44.

As seen in FIG. 1, a portion of the probe beam 22 passes directly through beam splitter 24 to strike incident power detector 56. As is well known to those skilled in the art, incident power detector 56 is provided to monitor fluctuations in the output power of the probe beam light source. The output of detector 56 is also supplied to the processor to provide normalization.

In accordance with the subject invention, at least one of the waveplate 40 or polarizer 44 are rotated to provide additional measurement information. In one preferred embodiment, it is the waveplate that is rotated. As used herein, the term "rotated" means that the orientation of the element is rotated about the azimuth (propagation axis of the probe beam) so that measurements can be taken at different azimuthal positions. Rotation can include continuous rotation as well as incremental or stepped rotation. In either case, it is preferable to take measurement at a large number of positions, for example, about 16 locations about the 360 degree axis. If a smaller number of increments are used, the device will still be operable, however, less data will be collected and the analysis would typically be less accurate. Various forms of stepper motors (not shown) can be used to rotate the compensator (or polarizer).

The analysis which is used in a rotating compensator device differs from a rotating polarizer in that there are additional higher order terms ("four omega terms") that provide more information. An example of the equations used to analyze data from a rotating compensator device are disclosed in U.S. Pat. No. 5,877,859 in the context of thin film analysis using Fourier coefficients. The general analysis would be the same herein. In accordance with the subject invention, the processor analyzes the data from the two dimensional array with selectable azimuthal orientations. More specifically, and with reference to FIG. 2, the processor can select the output from any detector element at any azimuthal orientation with respect to the detector and analyze the data as a function of the rotational orientation of the compensator. The location of the detector element can be mapped to the angle of incidence of the light on the sample.

In practice, the output of more than one detector element (at a plurality of compensator positions) would be analyzed. Typically, this data would be fitted to a model of the sample using an iterative process of the type well known in the art. More specifically, a theoretical model of the sample would be created which included the substrate, upper layers and any physical geometry. The model would be seeded with initial parameters. Theoretical reflectivities would be calculated based on the seed parameters using Fresnel and/or Maxwell's equations. The calculated results are compared to the actual measured data. To the extent that the measured data and the generated theoretical data do not match, the parameters supplied to the model are changed and the theoretical data regenerated. This process is repeated iteratively until the calculated data matches the actual measured data to a desired goodness of fit. Alternatively, libraries of possible solutions can be created. The measured data is compared to the generated data in the library to evaluate the sample.

The most complete analysis would be to use the output of all the elements in the two dimensional array. This approach would likely be too time consuming and too calculation intensive. Accordingly, the output of various subsets of detector elements could be used.

In one preferred approach, the outputs of elements lying along particular azimuthal directions on the detector (at a plurality of compensator positions) could be used. For example, the output of the detector elements lying along azimuthal direction A1 could be used in combination with the elements lying along azimuthal direction A2. The ability to select elements from any azimuthal direction can be very useful in a real life situation. For example, some test pads with geometrical features have known XY anisotropies. These might be measurable with only two linear arrays of detectors, provided that the arrays were aligned with the axes of the feature. In contrast, using the subject approach, there is no need to align the sample with the optics of the tool. Rather, an imaging system could be used to determine the orientation of the feature. That information could be supplied to the processor for selection of the most appropriate azimuthal angles on the detector.

Alternatively, the processor can be arranged to perform calculations along a number of different azimuthal directions, including for example, A3. The number of azimuthal directions is only limited by the resolution of the detector. Based on the calculation, a determination could be made about the orientation of the feature and then the parameters of the feature could be determined using conventional fitting algorithms known in the prior art.

Another approach would be to use the output of the pixels lying within an annulus or a certain radius from the center of the array. Data taken from the elements lying within the annulus (at a plurality of compensator positions) would provide a full range of azimuthal angles but with less computational strain than if the elements in the entire array were processed.

In addition to analyzing individual pixels and the associated angles of incidence, it would also be possible to use any of the integrated approaches described in U.S. Pat. No. 6,678,046. For example, four or eight pie shaped segments could be mapped onto the detector array. The outputs from each segment (at a plurality of compensator positions) could be summed and processed to derive an integrated measurement. This integrated approach could also be applied to detectors falling within an annulus or within segments such as shown in A1 and A2 in FIG. 2 (see, FIGS. 4, 5 and 6 of U.S. Pat. No. 6,678,046). It should be noted that since each detector element of the array has a physical size, some angle of incidence integration always exists even when using the output of individual elements.

As noted above, while it is preferable to use a rotating compensator to obtain the information, it is also possible to rotate a polarizer. In addition, one can use a pair of compensators, before and after the sample, with one or both being rotated. Similarly, one can use a pair of polarizers, before and after the sample, with one or both being rotated.

In the illustrated embodiment, the detector is shown measuring light reflected from the sample. The invention could also be implement in transmission if the sample was at least partially transmissive to the probe beam light. In this case, the detector would be located on the opposite side of the sample with respect to the light source.

It is often desirable to obtain measurements at more than one wavelength. If it is desired to measure with a very small spot size such that a laser light source is required to generate a coherent beam, light source 20 could be comprised of two or more lasers each having an output at different wavelengths. These lasers could be energized sequentially to produce data at different wavelengths. Alternately a wavelength tunable laser could be used.

Light source 20 could also be a white light source that would generate a polychromatic probe beam. A wavelength selective filter 60 (shown in phantom line in FIG. 1) would then be placed somewhere in the light path between the light source and the detector. The filter could take the form of simple band pass (color) filters which are selectively moved into the path of the beam. Alternatively, a monochrometer could be used to sequentially select narrow wavelength regions.

In U.S. Pat. No. 5,042,951, cited above, the elements in the photoarray were mapped to the angles of incidence as a function of sin of the angle of incidence. In these systems, an image of the sample at the focal plane of the lens 26 is relayed and imaged on the detector. Typically, an additional lens and a spatial filter (not shown here) are used.

As an alternative, a Fourier transform lens system could be used which allows mapping of the elements as a function of the tangent of the angle of incidence. This approach tends to increase the resolution at higher angles of incidence, a region where higher sensitivity is often available. See for example, "A New Analysis Strategy for CD Metrology Using Rapid Photo Goniometry Method," Petit, et al, SPIE Vol. 5375, pp. 210-221, February 2004, and "Innovative Rapid Photo-goniometry Method for CD Metrology," Boher, et. al., SPIE Vol. 5375, pp. 1302-1313, February 2004.

In situations where diffracting structures are to be measured, it may be desirable to set up the optics so that the ratio of scattered light detected compared to specularly reflected light detected is maximized. Various approaches for achieving that goal are described in U.S. patent application No. 2004/0004726. In one example, a baffle 70 (shown in phantom in FIG. 1) may be positioned across a portion of the beam path. Light which enters the left hand side of the lens and is specularly reflected and exits through the right hand side of the lens will be blocked from reaching the detector by baffle 70. In addition, light from the source directed towards the right hand side of the lens is blocked from reaching the lens and therefore does not emerge as specularly reflected light from the left hand side of the lens. Light entering the left hand side of the lens which is scattered can emerge from the left hand side of the lens and reach the detector.

A similar result can be achieved if the optics are set up so that the numerical aperture of illumination is less than the numerical aperture of detection. In this case, information related to specularly reflected light can be reduced by ignoring the output from detectors in the path of the specularly reflected light or by using a blocking member at that location (shown as 164 in FIG. 5B of the above cited patent application).

While the subject invention has been described with reference to a preferred embodiment, various changes and modifications could be made therein, by one skilled in the art, without varying from the scope and spirit of the subject invention as defined by the appended claims

I claim:

1. An apparatus for evaluating a sample comprising:
   a laser for generating a probe beam of radiation;
   a focusing element for focusing the beam onto the surface of the sample in a manner to create a spread of angles of incidence with varying azimuthal angles, said focusing element having a numerical aperture of at least 0.5;
   a rotatable retarder located in the path of the beam;
   a polarizer located in the path of the reflected beam;

a detector defined by a two dimensional array of photodetector elements for measuring the beam after reflection from with the sample, each element generating an output signal; and a processor for receiving the output signals from the detector and for controlling and monitoring the rotational position of the retarder about the propagation axis of the probe beam, said processor for evaluating the sample using the output signals of certain photodetector elements lying along a particular azimuthal direction with respect to the beam.

2. An apparatus as recited in claim 1, wherein the processor analyzes the sample using output of the elements lying along at least three different azimuthal directions with respect to the beam.

3. An apparatus for evaluating a sample comprising:
a light source for generating a probe beam of radiation;
a focusing element for focusing the beam onto the surface of the sample in a manner to create a spread of angles of incidence with varying azimuthal angles;
a rotatable retarder located in the path of the beam;
a polarizer located in the path of the beam after interaction with the sample;
a detector defined by a two dimensional array of photodetector elements for measuring the beam after interaction with the polarizer, each element generating an output signal; and
a processor for receiving the output signals from the detector and for controlling and monitoring the rotational position of the retarder about the propagation axis of the probe beam, said processor for mapping the location of elements of the detector to particular angles of incidence on the sample and evaluating the sample using the mapped output signals of a plurality of selected photodetector elements generated at a plurality of rotational positions of the retarder.

4. An apparatus as recited in claim 3, wherein the selected photodetector elements lie along more than one azimuthal direction of the beam.

5. An apparatus as recited in claim 3, wherein the light source is a laser.

6. An apparatus as recited in claim 3, wherein the focusing element has a numerical aperture of at least 0.5.

7. An apparatus as recited in claim 3, wherein the light source generates output radiation at more than one wavelength and the detector measures the probe beam at more than one wavelength.

8. An apparatus as recited in claim 7, wherein the sample is illuminated with different wavelengths sequentially and the measurements at different wavelengths are made sequentially.

9. An apparatus as recited in claim 8, wherein the light source is a tunable laser.

10. An apparatus as recited in claim 8, wherein the light source is a white light source the output of which is sequentially passed through a plurality of color selecting filters.

11. An apparatus as recited in claim 3, wherein the light source is a broadband light source and measurements are made at different wavelengths simultaneously.

12. An apparatus as recited in claim 3, wherein a group of the selected photodetector elements lie along one azimuthal direction.

13. An apparatus as recited in claim 3, wherein a group of the selected photodetector elements have an annular configuration.

14. An apparatus as recited in claim 3, wherein an image of the sample at the focal plane of the focusing element is relayed and imaged onto the detector.

15. An apparatus as recited in claim 3, further including a Fourier transform lens system to allow mapping of the photodetector elements as function of the tangent of the angle of incidence on the sample.

16. An apparatus as recited in claim 3, further comprising a baffle positioned across a portion of the beam path in a manner to increase the amount of scattered light being monitored in comparison to the amount of specularly reflected light being monitored.

17. A method for evaluating a sample comprising the steps of
focusing a probe beam onto the surface of the sample in a manner to create a spread of angles of incidence with varying azimuthal angles;
using a two-dimensional array of photodetecting elements, monitoring the probe beam after reflection from the sample, with each of the photodetecting elements generating an output signal;
passing the probe beam through a retarder and a polarizer prior to reaching photodetecting elements;
rotating the retarder about the propagation axis of the beam; and
evaluating the sample based on the output signals of selected ones of said photodetector elements and based on information about the rotational position of the retarder.

18. A method as recited in claim 17, wherein the selected photodetector elements lie along more than one azimuthal direction of the beam.

19. A method as recited in claim 17, wherein the probe beam is focused by a focusing element which has a numerical aperture of at least 0.5.

20. A method as recited in claim 17, wherein the sample is illuminated with the probe beam at different wavelengths sequentially and measurements at different wavelengths are made sequentially.

21. An method as recited in claim 17, wherein the probe beam comprises broadband radiation and measurements at different wavelengths are made simultaneously.

22. A method as recited in claim 17, wherein the probe beam is focused by a focusing element and an image of the sample at the focal plane of the focusing element is relayed and imaged onto the detector.

23. A method as recited in claim 17, further including the step of using a Fourier transform lens system to map the photodetector elements as function of the tangent of the angle of incidence on the sample.

24. A method as recited in claim 17, further comprising the step of blocking a portion of the probe beam path in a manner to increase the amount of scattered light being monitored in comparison to the amount of specularly reflected light being monitored.

* * * * *